US005656615A

United States Patent [19]

Camden

[11] Patent Number: 5,656,615
[45] Date of Patent: Aug. 12, 1997

[54] PHARMACEUTICAL COMPOSITION FOR INHIBITING THE GROWTH OF CANCERS AND VIRUSES IN MAMMALS

[75] Inventor: James Berger Camden, West Chester, Ohio

[73] Assignee: The Procter & Gamble Company, Cincinnati, Ohio

[21] Appl. No.: 420,935

[22] Filed: Apr. 12, 1995

[51] Int. Cl.$^6$ .............. A61K 31/66; A61K 31/325
[52] U.S. Cl. .............. 514/76; 514/114; 514/476; 514/485; 558/169; 558/234; 558/235; 558/241; 560/30; 562/17
[58] Field of Search .............. 514/76, 114, 476, 514/485; 558/169, 234, 235, 241; 560/30; 562/17

[56] References Cited

U.S. PATENT DOCUMENTS

| | | | |
|---|---|---|---|
| 2,695,225 | 11/1954 | Witman | 71/2.4 |
| 2,734,911 | 2/1956 | Strain | 260/471 |
| 3,799,758 | 3/1974 | Franz | 71/86 |
| 3,853,530 | 12/1974 | Franz | 71/76 |
| 3,903,297 | 9/1975 | Robert | 424/305 |
| 4,408,052 | 10/1983 | Hozumi | 546/22 |
| 4,542,219 | 9/1985 | Hozumi | 546/22 |
| 4,544,512 | 10/1985 | Hozumi et al. | 260/925 |
| 4,649,203 | 3/1987 | Hojima | 548/112 |
| 4,775,758 | 10/1988 | Hojima | 546/22 |
| 4,866,059 | 9/1989 | Temple | 514/248 |
| 5,114,951 | 5/1992 | King | 514/290 |

OTHER PUBLICATIONS

NASR "Computer Assisted Structure–Anticancer Activity" *Journal of Pharmaceutical Science* 74(8) pp. 831–836 Aug. 1985.

Zilkah "Effect of Inhibitors of Plant Cell Division on Mamalian Tumor Cells" *Cancer Research* 41, 1879–1883 May 1981.

U.S. Patent Application Ser. No. 08/420,913, J.B. Camden, filed Apr. 12, 1995.

U.S. Patent Application Ser. No. 08/420,914, J.B. Camden, filed Apr. 12, 1995.

Zilkah, et al, Proc. Am. Assoc. Cancer Res., vol. 22, 270 (1981).

Dialog, Elsevier Science Publishers, Abst. No. 212600, XP002011351 of Brown et al, J. Cell Biol., vol. 16, No. 2, 514–536 (1974).

Dus et al, Arch. Immunol. Ther. Exp., vol. 33, No. 219, 325–329 (1985).

Bandurina, et al., Pharm. Chem. J., vol. 12, No. 219, 325–329 (1985).

Mochida, et al., Trop. Agric. Res. Ser., vol. 19, 195–208 (1985).

*Primary Examiner*—David Buttner
*Attorney, Agent, or Firm*—Rose Ann Dabek; Jacobus C. Rasser

[57] ABSTRACT

This invention is a pharmaceutical composition that inhibits the growth of cancers and tumors in mammals, particularly in human and warm blooded animals. The composition contains a 10:1 to 1:10 mixture of (1) N-chlorophenyl carbamates and N-chlorophenylthiocarbamates and (2) N-phosphonoglycine derivatives which are systemic herbicides. This composition can also be used to treat viral infections.

24 Claims, No Drawings

PHARMACEUTICAL COMPOSITION FOR INHIBITING THE GROWTH OF CANCERS AND VIRUSES IN MAMMALS

TECHNICAL FIELD

This invention is a pharmaceutical composition that inhibits the growth of cancers and tumors in mammals, particularly in human and warm blooded animals. The composition contains a mixture of (1) N-chlorophenyl carbamates and N-chlorophenylthiocarbamates and (2) N-phosphonoglycine derivatives which are systemic herbicides. This composition can also be used to treat viral infections.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used.

Clearly, the development of materials that would target tumor cells due to some unique specificity for them would be a breakthrough. Alternatively, materials that were cytotoxic to tumor cells while exerting mild effects on normal cells would be desirable.

Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and a N-chlorophenylcarbamate or N-chlorophenylthiocarbamate derivative in combination with a N-phosphonoglycine derivatives as defined herein, along with a method of treating such cancers.

These compositions are also effective against viruses. Therefore it is a further object of this invention to provide a composition for and a method of treating viral infections such as herpes, HIV, influenza and rhinoviruses.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount anti-cancer compound selected from the group consisting of a mixture of (1) N-phosphonoglycine derivatives of the formula:

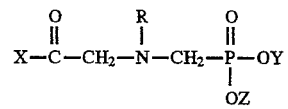

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetates, salicylates, pyridine, ammonium, lower aliphatic hydrocarbon amine, lower alkanol and aniline; and (2) N-chlorophenyl-carbamates and N-chlorophenylthiocarbamates of the formula:

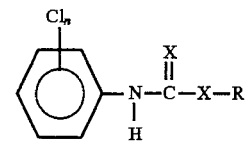

wherein X is oxygen or sulfur; n is from 1 to 3; R is selected from the group consisting of hydrogen, lower alkyl and lower alkenyl, cyclohexyl, phenalkyl of up to 8 carbon atoms, and phenyl, and the pharmaceutical acceptable organic and inorganic acid salts thereof.

These compositions can be used to inhibit the growth of cancers and other malignant tumors in humans or animals by administration of an effective amount of the N-phosphonoglycine derivatives and the N-chlorophenyl carbamates and N-chlorophenylthiocarbamates either orally, rectally, topically or parenterally, intravenously, or by direct injection near or into the tumor. These compositions are effective in killing or slowing the growth of tumors, yet are safer than adriamycin on normal, healthy cells.

These compositions are also effective against viruses, such as HIV, herpes, influenza and the like.

DETAILED DESCRIPTION OF THE INVENTION

A. DEFINITIONS

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" includes a pharmaceutically acceptable salt of the anti-cancer compound. These include acid salts of the amines and alkali or alkaline earth metal salt of the carboxylic acids.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or tumors found in mammals.

As used herein, the "anti-cancer compounds" are N-phosphonoglycines in combination with N-chlorophenylcarbamates and N-chlorophenylthiocarbamates.

As used herein, "viruses" include viruses which cause disease (viral infections) in warm blooded mammals, e.g., HIV, herpes, influenza, rhinoviruses, and the like.

B. THE ANTI-CANCER COMPOUNDS

The anti-cancer compounds are a combination of (1) N-phosphonoglycines and (2) N-chlorophenylcarbamates and N-chlorophenylthio carbamates which are known for their herbicidal activities. They are systemic herbicides used to prevent and eradicate certain plants or weeds or to regulate plant growth. The carbamates have the following structure

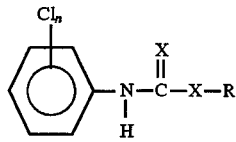

wherein n is from 1 to 3; R is selected from the group consisting of hydrogen, lower alkyl and lower alkenyl, cyclohexyl, phenalkyl of up to 8 carbon atoms, phenyl, and X is sulfur or oxygen; and the pharmaceutical addition salts of these compounds.

Preferred compounds are those in which R is alkyl with 1 to 4 carbons, preferably, isopropyl and X is oxygen.

These compounds are prepared by the methods described in U.S. Pat. No. 2,695,225 issues to Witman (1954) and in U.S. Pat. No. 2,734,911 issued to Strain (1956).

The N-phosphonoglycines have the formula:

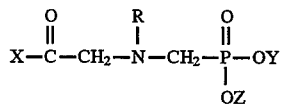

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, salicylate, pyridine, ammonium, lower aliphatic hydrocarbon amine, lower alkanol amine and aniline.

The N-phosphonoglycine compounds are prepared according to the method found in U.S. Pat. No. 3,799,758 issued to Franz (1974).

The mixture of the (1) N-phosphonoglycines and (2) the N-chlorophenylcarbamates and the N-chlorophenylthiocarbamates compounds is in a ratio of 10:1 to about 1:10 relative to each other on a mole weight basis. Preferably a ratio of 5:1 to 1:5 is used, and most preferred a 1:1 mixture.

C. DOSAGE

Any suitable dosage may be given in the method of the invention. The type of compound and the carrier and the amount will vary widely depending on the species of the warm blooded animal or human, body weight, and tumor being treated. Generally a dosage of between about 2 milligrams (mg) per kilogram (kg) of body weight and about 400 mg per kg of body weight is suitable. Preferably from 15 mg to about 150 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical or parenteral administration or intravenous injection or by injection into or around the tumor site.

D. DOSAGE DELIVERY FORMS

The anti-cancer compounds are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include aqueous solutions, solutions or suspensions in water, pharmaceutically acceptable fats or oils, alcohols or other organic solvents, including esters, elixirs, syrups, emulsions, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, and melting agents. Oral dosage forms would contain flavorants and coloring agents. Parenteral and intravenous forms would also include minerals and other materials to make them compatible with the type of injection or delivery system chosen.

Specific examples of pharmaceutically acceptable carriers and excipients that may be used to formulate oral dosage forms of the present invention are described in US. Pat. No. 3,903,297 to Robert, issued Sep. 2, 1975. Techniques and compositions for making dosage forms useful in the present invention are described in the following references: 7 *Mod-* ern *Pharmaceutics*, Chapters 9 and 10 (Banker & Rhodes, Editors, 1979); Lieberman et al., *Pharmaceutical Dosage Forms: Tablets* (1981 ); and Ansel, *Introduction to Pharmaceutical Dosage Forms* 2nd Edition (1976).

E. METHOD OF TREATMENT

The method of treatment can be any suitable method which is effective in the treatment of the particular virus, cancer or tumor type that is being treated. Treatment may be oral, rectal, topical, parenteral, intravenous or injection into or around the tumor site and the like. The method of applying an effective amount also varies depending on the tumor being treated. It is believed that parenteral treatment by intravenous or subcutaneous, or intramuscular application, formulated with an appropriate carrier, additional cancer inhibiting compound or compounds or diluent to facilitate application will be the preferred method of administering the compounds to warm blooded animals.

The method of treating viral infections may also be by oral, rectal, parenteral, topical or intravenous administration. The actual time and dose administration is dependent on the type of viral infection, the type of administration and the blood level desired.

The following examples are illustrative and are not meant to be limiting to the invention.

Colon, Breast and Lung Tumor Cells Test

The following cell culture tests were performed to test the toxicity of N-chlorophenylcarbamates and N-chlorophenylthiocarbamates compounds on colon, breast and lung human tumor cells. The viability of the cells were tested by looking at MTT (3-[4,5-dimethylthiazol-2-yl]-2, 5-diphenyltetrazolium bromide) reduction MTT assay is a well known measure of cell viability.

The colon tumor cells (HT29 from American Type Culture Collection (ATCC)) and the breast cells (MX1 from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37°±1° C. in of humidfied atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0.45 micrometer filter to remove undissolved crystals. The medium was decanted from the wells of the bioassy plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells and test article wells, respectively, to give the corresponding mean $OD_{550}$.

$$\% \text{ of Control} = \frac{\text{corrected mean } OD_{550} \text{ of Test Article Dilution}}{\text{corrected mean of } OD_{550} \text{ of Solvent Control}} \times 100$$

Dose response curves were prepared as semi-log plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin. The EC-50 is the concentration at which one half the cells are killed.

TABLE 1

| Test Material | EC-50 Result (ppm) | | | | | |
|---|---|---|---|---|---|---|
| | HT29 | HT29 | MX1 | MX1 | A549 | A549 |
| Adriamycin | 0.003 | 0.006 | 0.02 | 0.001 | 0.03 | 0.009 |
| chloroprofam ® | 13.3 | 11.4 | 91.8 | 108 | 12.6 | 92.5 |
| glyphosate | 5.41 | 3.73 | 36.5 | 14.6 | 25.9 | 22.3 |
| 1:1 mixture* | 1.96 | 1.61 | 9.70 | 8.78 | 10.8 | 10.1 |

*a mixture of chloropropham ® and glyphosate ®. Glyphosate or N-(phosphonomethyl) glycine is produced ny Monsanto. The mono (isopropylamine) salt is sold as a broad spectrum herbicide. Chloropropham is (3-Chlorophenyl) carbamic acid 1-methylethyl ester or m-chlorocarbanilic acid isopropyl ester. This material is sold as a herbicide or a plant growth regulator.

In normal healthy cells, the following results were obtained:

TABLE 2

| Test Material | EC-50 | | | | | |
|---|---|---|---|---|---|---|
| | Broncheal Cells Fibroblasts | | Kerotinoyle Cells | | | |
| chloro-profam® | 0.002 | >15.2 | 3.9 | 13.0 | >152 | 64.2 |
| glyphosate | 1.59 | 3.54 | 3.09 | 3.21 | 86.1 | 35.8 |
| 1:1 mixture* | 0.001 | 0.497 | 0.242 | 0.286 | 129 | 5.95 |
| Adriamycin | 0.015 | 0.0020 | 0.0035 | 0.0093 | 0.065 | 0.10 |

*a mixture of chlorophropham® and glyphosate®

These experiments show that these compositions are effective in killing tumor cells without significantly affecting healthy cells.

It is believed that many systemic herbicides alone or in combination with other herbicides and fungicides will slow this beneficial anti-tumor effect.

The mixture of (1) the N-phosphonoglycines and (2) N-chlorophenyl-carbamates and N-chlorophenylthiocarbamates are also effective against viruses including rhinovirus, HIV, herpes, and influenza.

What is claimed is:

1. A pharmaceutical composition for treating cancers and viral infections comprising a safe and effective amount of a mixture of.

(1) a carbamate compound of the formula:

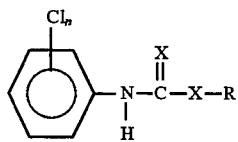

wherein n is from 1 to 3; X is selected from the group consisting oxygen and sulfur and wherein R is selected from the group consisting of hydrogen, lower alkyl and lower alkenyl, cyclohexyl, phenalkyl of up to 8 carbon atoms and the pharmaceutically acceptable salts of these compounds; and a (2) N-phosophonoglycine of the formula:

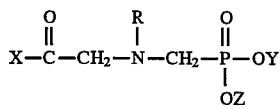

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, salicylate, pyridine, ammonium, lower aliphatic hydrocarbon amine, lower alkanol amine and aniline.

2. A pharmaceutical composition according to claim 1 comprising a pharmaceutically acceptable carrier and a safe and effective amount of N-phosphonoglycine derivatives and a carbamate compound.

3. A pharmaceutical composition according to claim 2 wherein said pharmaceutical acceptable acid addition salts are selected from the group consisting of hydrochloride, acetate, salicylate and mixtures thereof.

4. A method of treating cancer in warm blooded mammals comprising administering a safe and effective amount of a pharmaceutical composition comprising a mixture of:

(1) N-phosphonoglycine derivative of the formula:

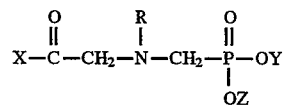

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyelohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, pyridine, ammonium, lower aliphatic hydrocarbon amine, lower alkanol amine or aniline; and (2) a carbamate compound of the formula:

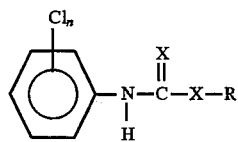

wherein n is from 1 to 3, X is selected from the group consisting of oxygen and sulfur and R is selected from the group consisting of hydrogen, lower alkyl and lower alkenyl, cyclohexyl, phenalkyl of up to 8 carbon atoms, phenyl, or the pharmaceutically acceptable addition salts of these compounds.

5. A method of treating cancer in warm blooded mammals according to claim 4 comprising administering a safe and effective amount of the composition wherein R of the carbamate compound is alkyl of from 1 to 4 carbons.

6. A method according to claim 5 wherein from about 2 mg/kg body weight to about 400 mg/kg of said mixture is administered.

7. A method according to claim 6 wherein said mixture is administered orally or enterically, intravenously, parenterally or by injection into or around the tumor site.

8. A method according to claim 7 wherein said mixture is administered in a solid form.

9. A method according to claim 8 wherein said solid form includes a carrier selected from the group consisting of lactose, sucrose, gelatin and agar.

10. A method according to claim 9 wherein from about 15 mg/kg to about 150 mg/kg of said mixture is administered.

11. A method according to claim 7 wherein said mixture is administered in a liquid form.

12. A method according to claim 11 wherein said liquid dosage from is selected from the group consisting of aqueous solutions, emulsions, suspension solutions, and suspensions reconstituted from non-effervescent and effervescent preparations.

13. A method according to claim 12 wherein said liquid dosage from a member selected from the group consisting of suspending agents, diluents, sweeteners, flavorants, colorants, preservatives, emulsifying agents and coloring agents, and mixtures thereof.

14. A unit dosage composition for treating cancer, tumors and viral infections comprising a safe and effective amount of a mixture of:

(1) a carbamate compound of the formula:

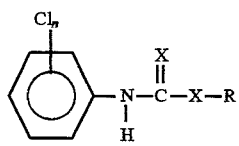

wherein X is selected from the group consisting of oxygen and sulfur, n is from 1 to 3 and R is selected from the group consisting of hydrogen, lower alkyl and lower alkenyl, cyclohexyl, phenalkyl of up to 3 carbon atoms, phenyl, or pharmaceutically acceptable addition salts thereof; and (2) a N-phosphonoglycine of the formula:

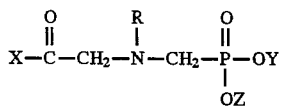

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, salicylate, pyridine, ammonium, lower aliphatic hydrocarbon amine, lower alkanol amine or aniline.

15. A unit dosage composition according to claim 14 wherein said carbamate is (3-chlorophenyl)carbamic acid 1-methylethyl ester.

16. A unit dosage composition according to claim 14 wherein said pharmaceutical acceptable acid addition salts are selected from the group consisting of hydrochlorides, acetates, salicylates or mixtures thereof.

17. A method of treating viral infections in warm blooded mammals comprising administering a safe and effective amount of a pharmaceutical composition comprising a mixture of:

(1) N-phosphonoglycine derivatives of the formula:

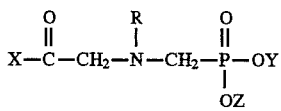

wherein X is selected from the group consisting of hydroxy, alkoxy or chloroxy up to 12 carbon atoms; lower alkenoxy, cyelohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, pyridine, ammonium, lower aliphatic hydrocarbon amine, lower alkanol amine and aniline; and (2) a carbamate compound of the formula:

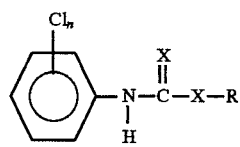

wherein n is from 1 to 3, X is selected from the group consisting of oxygen and sulfur and R is selected from the group consisting of hydrogen, lower alkyl and lower alkenyl, cyclohexyl, phenalkyl of up to 8 carbon atoms, phenyl, and the pharmaceutically acceptable addition salts of these compounds.

18. A method of treatment according to claim 17 wherein said mixture is administered orally or enterically, intravenously, parenterally or by injection.

19. A method of treatment according to claim 18 wherein said mixture is administered in a solid form.

20. A method of treatment according to claim 19 wherein said solid form includes a carrier selected from the group consisting of lactose, sucrose, gelatin and agar.

21. A method of treatment according to claim 18 wherein from about 15 mg/kg to about 150 mg/kg of said mixture is administered.

22. A method of treatment according to claim 18 wherein said mixture is administered in a liquid form.

23. A method of treatment according to claim 22 wherein said liquid dosage from is selected from the group consisting of aqueous solutions, emulsions, suspension solutions, and suspensions reconstituted from non-effervescent and effervescent preparations.

24. A method of treatment according to claim 23 wherein said liquid dosage form contains a member selected from the group consisting of suspending agents, diluents, sweeteners, flavorants, colorants, preservatives, emulsifying agents and coloring agents, and mixtures thereof.

* * * * *

UNITED STATES PATENT AND TRADEMARK OFFICE
CERTIFICATE OF CORRECTION

PATENT NO.    : 5,656,615
DATED         : August 12, 1997
INVENTOR(S)   : James Berger Camden It is certified that error appears in the above-identified patent and that said Letters Patent is hereby corrected as shown below:

Column 2,
Line 12, delete "chloroxy" and insert in lieu thereof -- chloralkoxy --.
Line 13, delete "pyrrlidinyl" and insert in lieu thereof -- pyrrolidinyl --.

Column 3,
Line 62, delete "chloroxy" and insert in lieu thereof -- chloralkoxy --.
Line 63, delete "pyrrlidinyl" and "viral", and insert in lieu thereof -- pyrrolidinyl --.

Column 7,
Line 27, delete the period ".".
Line 37, insert -- of -- immediately after "consisting".
Line 37, insert a semicolon -- ; -- immediately after "sulfur".
Lines 38 and 56, insert a comma -- , -- immediately after "alkyl" and delete "and".
Line 39, delete "and" and insert in lieu thereof -- ; or --.
Line 50, delete "chloroxy" and insert in lieu thereof -- chloralkoxy --.
Line 50, delete the semicolon after "atoms" ";" and insert in lieu thereof a comma -- , --.
Line 51, delete "pyrrlidinyl" and insert in lieu thereof -- pyrrolidinyl --.
Line 52, immediately after "Z", insert -- are --.
Line 58, immediately after "anisyl;", delete "and" and insert in lieu thereof -- or --.
Line 65, immediately before "comprising", insert -- further --.
Lines 65-67, delete "and a safe and effective amount of N-phosphonoglycine derivatives and a carbamate compound".

Column 8,
Line 2, delete "pharmaceutical" and insert in lieu thereof -- pharmaceutically --.
Line 2, delete "acid addition".
Line 16, delete "chloroxy" and insert in lieu thereof -- chloralkoxy --.
Line 16, delete the semicolon after "atoms" ";" and insert in lieu thereof a comma -- , --.
Line 17, delete "pyrrlidinyl" and insert in lieu thereof -- pyrrolidinyl --.
Line 18, immediately after "Z", insert -- are --.
Lines 22 and 40, insert a comma -- , -- immediately after "alkyl" and delete "and".
Line 24, immediately after "anisyl;", delete "and" and insert in lieu thereof -- or --.
Line 28, delete "or" immediately before "aniline", and insert in lieu thereof -- and --.
Line 39, insert a semicolon -- ; -- immediately after "sulfur".
Line 41, insert -- and -- immediately after "atoms,".
Line 42, delete the comma "," immediately after "phenyl" and insert in lieu thereof -- ; --.
Line 53, delete "into or around the tumor side".
Line 64, delete "from" and insert in lieu thereof -- form --.
Line 66, delete "and" and insert in lieu thereof -- or --.

UNITED STATES PATENT AND TRADEMARK OFFICE
CERTIFICATE OF CORRECTION

PATENT NO.  : 5,656,615  
DATED       : August 12, 1997  
INVENTOR(S) : James Berger Camden Page 2 of 3

It is certified that error appears in the above-identified patent and that said Letters Patent is hereby corrected as shown below:

Column 9,  
Line 2, delete "from a member" and insert in lieu thereof -- form is --.  
Line 4, delete "and" and insert in lieu thereof a comma -- , --.  
Line 20, insert a comma -- , -- immediately after "3".  
Lines 21 and 40, insert a comma -- , -- immediately after "alkyl" and delete "and".  
Line 22, insert -- and -- immediately after "atoms,".  
Line 22, delete the comma "," immediately after "phenyl" and insert in lieu thereof -- ; --.  
Line 33, delete "chloroxy" and insert in lieu thereof -- chloralkoxy --.  
Line 33, delete the semicolon after "atoms" ";" and insert in lieu thereof a comma -- , --.  
Line 34, delete "pyrrlidinyl" and insert in lieu thereof -- pyrrolidinyl --.  
Line 35, immediately after "Z", insert -- are --.  
Line 38, insert a comma -- , -- immediately after "hydrogen".  
Line 42, immediately after "anisyl;", delete "and" and insert in lieu thereof -- or --.  
Line 46, delete "or" immediately before "aniline", and insert in lieu thereof -- and --.  
Line 53, delete "pharmaceutical" and insert in lieu thereof -- pharmaceutically --.  
Line 53, delete "acid".  
Line 55, delete "or" and insert in lieu thereof -- and --.  
Line 59, delete the period ".".

Column 10,  
Line 1, insert -- an -- immediately after "(1)".  
Line 1, delete "derivatives" and insert in lieu thereof -- derivative --.  
Line 9, "chloroxy" and insert in lieu thereof -- chloralkoxy --.  
Line 9, delete the semicolon after "atoms" ";" and insert thereof a comma -- , --.  
Line 10, delete "pyrrlidinyl" and insert in lieu thereof -- pyrrolidinyl --.  
Line 11, immediately after "Z", insert -- are --.  
Lines 15 and 32, insert a comma -- , -- immediately after "alkyl" and delete "and".  
Line 17, immediately after "anisyl;", delete "and" and insert in lieu thereof -- or --.  
Line 31, insert a comma -- , -- immediately after "sulfur".  
Line 33, insert -- and -- immediately after "atoms,".

UNITED STATES PATENT AND TRADEMARK OFFICE
CERTIFICATE OF CORRECTION

PATENT NO.   : 5,656,615
DATED        : August 12, 1997
INVENTOR(S)  : James Berger Camden It is certified that error appears in the above-identified patent and that said Letters Patent is hereby corrected as shown below:

Column 10 cont'd,
Line 34, immediately after "phenyl", delete the comma "," and insert in lieu thereof, -- ; or --.
Line 50, delete "from" and insert in lieu thereof -- form --.
Line 52, delete "and" and insert in lieu thereof -- or --.
Line 57, delete "and" and insert in lieu thereof a comma -- , --.

Signed and Sealed this

Eighth Day of October, 2002

Attest:

JAMES E. ROGAN
Attesting Officer    Director of the United States Patent and Trademark Office